US008085904B2

(12) United States Patent
Pinault et al.

(10) Patent No.: US 8,085,904 B2
(45) Date of Patent: Dec. 27, 2011

(54) EMERGENCY COMMUNICATION METHOD, SERVER, NETWORK AND COMPUTER PROGRAM FOR SUCH COMMUNICATION

(75) Inventors: Francis Pinault, Bois-Colombes (FR); François Olivier, Plobsheim (FR)

(73) Assignee: Alcatel Lucent, Paris (FR)

( * ) Notice: Subject to any disclaimer, the term of this patent is extended or adjusted under 35 U.S.C. 154(b) by 1201 days.

(21) Appl. No.: 11/777,261

(22) Filed: Jul. 12, 2007

(65) Prior Publication Data

US 2008/0043933 A1    Feb. 21, 2008

(30) Foreign Application Priority Data

Jul. 13, 2006 (FR) .................................. 06 52955

(51) Int. Cl.
*H04M 11/04* (2006.01)

(52) U.S. Cl. ...................................... 379/45; 455/404.1

(58) Field of Classification Search .................. 379/45; 404/404.1
See application file for complete search history.

(56) References Cited

U.S. PATENT DOCUMENTS

| 6,697,468 | B2 * | 2/2004 | Wong et al. ............... 379/112.01 |
| 6,766,159 | B2 * | 7/2004 | Lindholm ................... 455/404.1 |
| 7,340,239 | B2 * | 3/2008 | Laatu ......................... 455/404.1 |
| 2002/0197977 | A1 | 12/2002 | Brooks | |

FOREIGN PATENT DOCUMENTS

| WO | WO 98/31168 A2 | 7/1998 |
| WO | WO 01/17302 A1 | 3/2001 |
| WO | WO 2004/057901 A1 | 7/2004 |

* cited by examiner

*Primary Examiner* — Creighton Smith
(74) *Attorney, Agent, or Firm* — Fay Sharpe LLP

(57) ABSTRACT

This method includes:
a step (1, 2A, 2B) of a server receiving a request from a calling terminal to set up a call between the calling terminal and an emergency call center, and
a step (5) of setting up a call between the calling terminal and the call center;
a step (2B, 8) of identifying, in the call set-up request, a type of event belonging to a list of predefined event types, such as medical problems, fire, etc.;
a step (9) of identifying a community having capabilities suited to the type of event identified; and
a step (11) of sending information to at least one terminal belonging to the community thus identified.
A preferred embodiment of the method further includes sending (11) at least one terminal belonging to the community thus identified the location of the calling terminal and the type of event identified.

10 Claims, 2 Drawing Sheets

EMERGENCY COMMUNICATION METHOD, SERVER, NETWORK AND COMPUTER PROGRAM FOR SUCH COMMUNICATION

The invention relates to the field of telecommunications. More precisely, it concerns the connection of two terminals, a calling terminal and a called terminal, typically a call center.

Call centers are PABX (Private Automatic Branch exchanges) rated for high volumes of dedicated traffic in such fields as financial markets, telemarketing, emergency services, on-line help or maintenance services, witness statement services, for example following abduction of a child.

The invention concerns in particular communications in the case of a sudden and generally unexpected event that requires immediate measures to minimize its harmful consequences. Such emergency situations cause stress for any witnesses as well as for participants in such events.

The efficacy of call centers (for example emergency call centers, Emergency Calling Services Enhanced 911 in the United States and in Canada, or 112 in Europe) is frequently reduced for the following reasons:

Partial or total lack of information on the location of the caller, who does not necessarily know exactly where he is himself. The caller's stress can also limit his ability to state his location clearly.

Lack of precise information given by the caller on the event that he wishes to report. This lack of information can be the result of the caller's stress, panic or turmoil, the caller failing to express himself or speaking incoherently.

The language of the caller: every year more than 100 million European citizens travel within the boundaries of the European Union (tourists, workers, persons living or working near national borders). A single emergency call number was established for the European Union in 1991. Thirteen years later, an evaluation of this service during preparations for the "Euro 2004" football championship in Portugal showed that 20% of calls in French and 29% of calls in English received no help at all (DECO 112 Service Survey Final Overall Report). The language barrier can be serious in the event of cross-border catastrophes.

Unnecessary calls: it is estimated that only 40% of calls to emergency call centers call for a response. The remaining 60% consist of requests for information, operations intended to test a device, for example a mobile telephone, calls from children playing, malicious acts and calls reporting events already known to the emergency services.

Saturation of the call center and redundant calls. In the event of calamities such as natural disasters or technological catastrophes, for example, call centers, and especially emergency call centers, are inundated with calls coming from witnesses, victims or their families. Thus the thousands of emergency call centers in the European Union receive some 200 million calls each year from citizens in distress: cardiovascular incidents, apoplexy, road traffic accidents, suicides, drownings, assaults, fires, falls, poisoning, terrorist acts. In this flood of calls, operators must distinguish those that are redundant from those reporting a new event or a change in respect of an event that has already been reported. Major events (for example financial crashes, coups, natural disasters, industrial accidents, airplane crashes) by their very nature affect a large number of persons and have multiple aspects and consequences. In these situations of rapidly changing crisis, call center operators would prefer not to receive information that they already have or that is obsolete, in order to concentrate their efforts on pertinent and up-to-date information. The success of mobile telephones has increased the risk of saturation of call centers, especially in the case of emergency call centers, and especially as in public mobile telephone networks, in particular GSM networks, an emergency connection can be set up even without the right of access to the network that covers the location, and even with no SIM (Subscriber Identity Module) card in the calling terminal. In 1995, there were 34 million mobile telephone users in the United States (source: Cellular Telecommunications and Internet Association) and emergency call centers received 20 million calls that year. The number of mobile telephone users in the United States is currently estimated at 116 million and the number of calls from a mobile telephone to emergency call centers is said to be of the order of 50 million a year.

All these problems can have the consequence of a serious delay before the arrival of emergency services at the site of the event that motivated a call. The response time is a decisive factor in a large number of emergency situations. Consequently, it is desirable also to call on private sector emergency services located near the site of the event, where this is possible. In any community, such as a company, there are often persons competent to give help. For example, a nurse employed by a company can rapidly assist a person who has suffered an accident or a heart attack. Any employee who has been trained as a voluntary firefighter can intervene rapidly if a fire should start. In the conventional way, a witness to an event calls the public sector emergency services by entering a standard number such as 112 in Europe or 911 in the USA. If a witness thinks of calling private sector emergency services (the sick bay or gatehouse of the company), he must have the appropriate number and make a second telephone call. This is neither very practical nor very fast.

A first object of the invention is to facilitate calling such private sector emergency services.

To this end, a first aspect of the invention relates to a method of communication between a calling terminal and an emergency call center via a call server to which said calling terminal and other terminals are connected, this method including:

a step of the server receiving a request from a calling terminal to set up a call between the calling terminal and an emergency call center, and a step of setting up a call between the calling terminal and the call center; and which is characterized in that it further includes:

a step of identifying, in the call set-up request, a type of event belonging to a list of predefined event types;

a step of identifying, in a set of communities with predefined capabilities and each having at least one terminal connected to said server, a community having capabilities suited to the type of event identified; and a step of sending information to at least one terminal belonging to the community thus identified.

A preferred embodiment of the invention further includes sending at least one terminal belonging to the community thus identified the location of the calling terminal and the type of event identified.

Dialing on the calling terminal to set up the request for communication with the emergency call centre preferably comprises entering a prefix assigned to the emergency call centre and entering a termination identifying a type of event.

One embodiment of the method further includes sending a message to all terminals within a particular perimeter around the location of the calling terminal. Sending such a message has numerous advantages. In particular, the message may dissuade witnesses to an event already reported to the emergency call center from calling the center. The risk of saturation of the call center is reduced commensurately. The message (text or audio) can also reassure other victims within the perimeter of the event already reported. The message can also reassure persons in the vicinity of the site of the event, and tell them what to do to assure their own safety.

In one embodiment, the calling terminal is mobile and the location data includes geolocation data obtained in particular by identifying a cell or a sector, estimating the times of arrival (TOA Time of Arrival, EOTD Enhanced Observed Time Difference TDOA), estimating angles of arrival (AOA) or angles of incidence.

Alternatively, the calling terminal is a mobile, in particular a GSM or UMTS mobile, provided with a GNSS receiver, such as a GPS, GLONASS or GALILEO receiver, the location data of the calling terminal including geolocation data.

A second aspect of the invention relates to a communication server including:
  means for receiving a request from a calling terminal to set up a call between the calling terminal and an emergency call center, and
  means for setting up a call between the calling terminal and the call center; and which is characterized in that it further includes:
  means for identifying, in the call set-up request, a type of event belonging to a list of predefined event types;
  means for identifying, in a set of communities with predefined capabilities and each having at least one terminal connected to said server, a community having capabilities suited to the type of event identified; and
  means for sending information to at least one terminal belonging to the community thus identified.

A preferred embodiment of this server is characterized in that it includes means for receiving the location of the calling terminal and in that the means for sending information include means for sending the location of the calling terminal and the type of event identified.

Other objects and advantages of the invention will become apparent in the light of the following description of embodiments of the invention given with reference to the appended drawings, in which.

By way of example only, the call center 5 referred to in the remainder of this description is the 112 call center. When the call center number is entered on the calling terminal, it is followed by at least one digit corresponding to the type of event to be reported to the call center.

For example:
  1121 is the number for a situation of personal danger, such as an assault;
  1122 is the number for a medical problem;
  1123 is the number for reporting a hazard such as a fire, when the caller is not in immediate danger.

Figure 1:
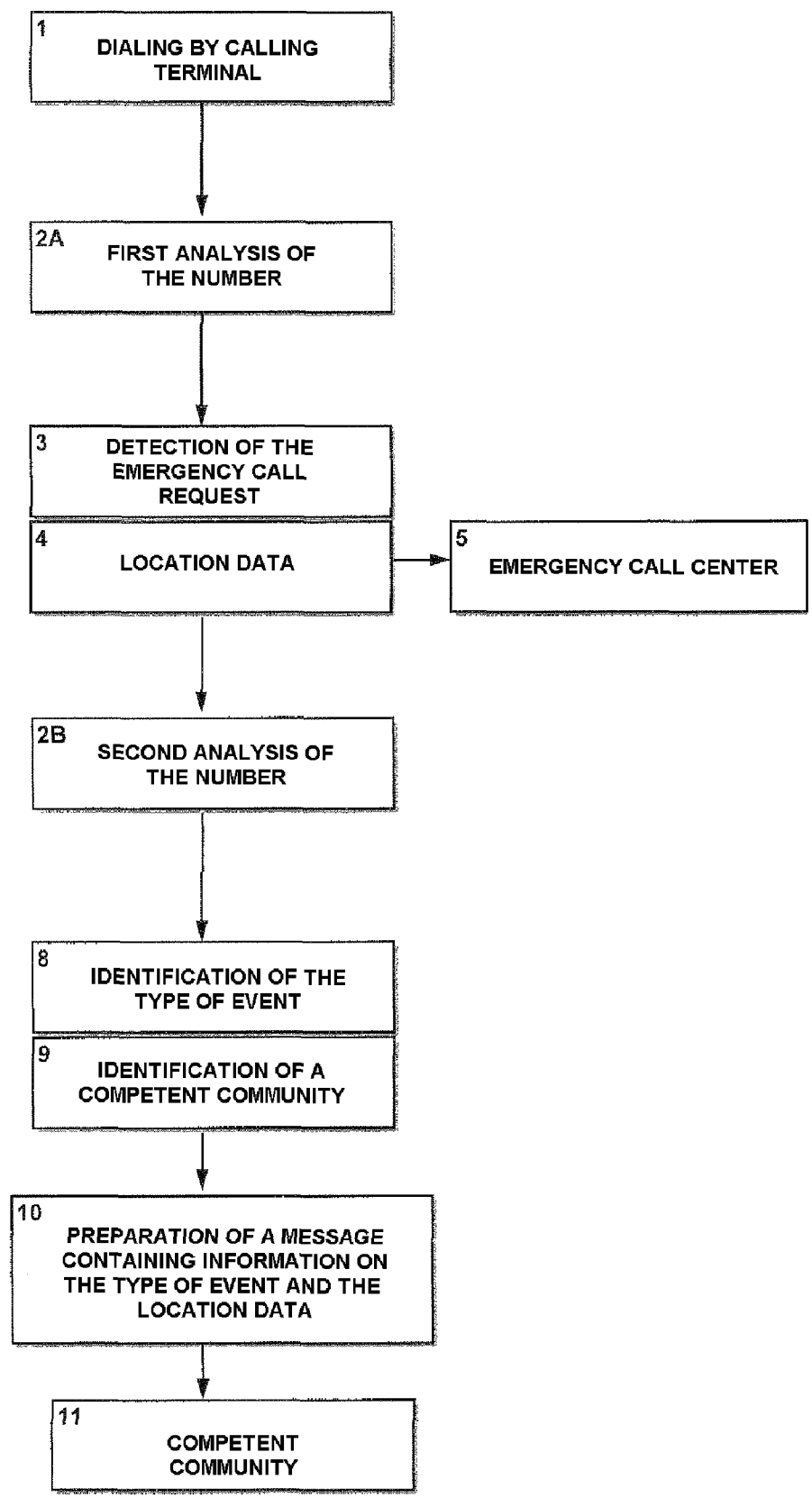
FIG. 1 is a diagram illustrating one embodiment of the method of the invention.

FIG. 1 is a flowchart showing one embodiment of the method of the invention.

Step 1: The call server of the invention receives a call set-up request that includes one of the predetermined numbers.

Step 2A: A first analysis of the number of the request separates the data contained in the request. In particular, the called number is extracted, after which the first portion of this number (the first three digits) is extracted and analyzed to detect if it is a call to an emergency call center.

Step 3: Detection of the number 112 identifying a call to an emergency call center.

Step 4: Detection of any location data in the request. If the calling terminal can give its location, the request advantageously contains location data for the calling terminal. The location of the calling terminal can be obtained by the following standard means if the calling terminal is a mobile terminal:
  a) identification of the cell (Cell ID) or the sector, by means of information available in the BTS (Base Transceiver Station) or from the sector that provides the service;
  b) triangulation, if a plurality of base transceiver stations pick up the call emanating from the mobile concerned. The signals employed for triangulation can be RXLEV (Reception Level) measurements that represent the power, as measured by the mobile telephone, of signals coming from certain base transceiver stations. In a first variant of triangulation, the time of arrival (TOA Time of Arrival, EOTD Enhanced Observed Time Difference TDOA) is estimated from the uplink signals (sent by the mobile and received by the BTS) or the downlink signals (signals sent to the mobile). In a second variant of triangulation, known as angle of arrival (AOA) or angle of incidence estimation, each estimated AOA defines a half-segment with the base transceiver station concerned at on end, on which the mobile telephone is located. Two AOA measurements are therefore necessary to locate the mobile. Alternatively, if angles and delays are estimated simultaneously, determining the location of the mobile telephone necessitates receiving from only one BTS;
  c) satellite location, for GSM (Global System for Mobile communications) terminals equipped with a GNSS (Global Navigation Satellite System) receiver, such as a GPS (Global Positioning System), GLONASS or GALILEO type receiver by means of which the mobile telephone picks up transmissions from satellites to determine its position. This location technique employs a plurality of satellites continuously transmitting a phase-modulated pseudo-random time-stamped signal. In a first step, called the acquisition step, the receiver determines pseudo-random codes modulating the signals coming from the satellites "in view" belonging to a constellation of positioning (for example GPS) satellites and related to a reference time that is generally called the system time. In this acquisition step, the signals received from the satellites "in view" are compared to signal replicas resulting from assumptions of the system time and the timing frequency of the satellites, in order to deduce therefrom the pseudo-random codes modulating the received signals. The receiver delays the beginning of this sending of code until its signal is superimposed on that coming from the satellite. The value of this delay is therefore the time taken by the signal to propagate from the satellite to the user. Each propagation time measurement represents the radius of a sphere centered on a particular satellite, the receiver being situated on that sphere. With two distance measurements, the position of a receiver is on a circle formed by the intersection of two spheres. A simultaneous third measurement reduces the intersection to two points, one of which is very far away in space and easily isolated. In an Assisted-GPS mode of operation, the position calculation employs a mobile device receiving and processing GNSS signals and communicating with a cellular network and an assistance data server responsible for broadcasting data for assisting the processing of the GNSS signals performed in the mobile. In an MS-assisted mode of operation, the server broadcasts data for assisting the measurement of pseudo-distances from the GPS signals, which measurements are then forwarded to the server, which calculates the position. To enhance the accuracy of the estimated positions, the constellations of positioning satellites are advantageously coupled to augmentation systems, of the SBAS (Satellite Based Augmentation System) type, comprising terrestrial stations and geostationary (for example IMMARSAT and ARTEMIS) satellites. SBAS messages are used to correct data provided by the positioning satellites, more particularly errors in temporal synchronization between navigation satellites and ephemeredes errors, propagation errors.

The location of the calling terminal can be obtained by the following means if the calling terminal is an IP software telephone (IP softphone):

1) the standard SNMP (Simple Network Management Protocol) supplies information to an LIS (Location Information Server) for identifying changes of MAC (Medium Access Control) addresses when ports are connected and disconnected. A capture mechanism (described in RFC 2863) updates changes in the Ethernet network in real time. The MIB (Management Information Base) enables an NMS (Network Message System) to monitor the MAC address assignment table. In a variant of this prior art concept, the LLDP-MED protocol (Link Layer Discovery Protocol-Media Endpoint Discovery) takes into account only changes in the assignment of ports for VoIP (Voice Over Internet Protocol) devices;

2) a DHCP (Dynamic Host Configuration Protocol) request is submitted using the SubOpt1 option of RFC 3046 (Relay Agent Information Option). An Ethernet switch adds its MAC address and the port number to the DHCP request;

3) a DHCP tracker supplies a DHCP client with location information corresponding to the port of the LAN (Local Area Network) to which it is connected. The DHCP tracker necessitates adding an option 123 to the DHCP request (DHCPDISCOVER) and receiving in the case of the same option the location data in the response of the server (DHCPOFFER).

Step 2B: A second analysis of the called number to extract the second portion of the called number (the fourth digit in this example).

Step 8: Identification of the type of emergency, for example: fire, medical emergency, etc., from the second portion of the called number (1, 2, 3, . . . ).

Step 9: The type of event identified determines a community within a set of communities having predefined capabilities (voluntary firefighters, medical services, rescue services, etc.) and each having at least one terminal connected to said server. In this example, the server also takes account of the location of the calling terminal. The server determines a community having capabilities suited to the type of event identified, where applicable reduced to a single person, and located closest to the calling terminal.

Step 10: After determining a competent community for this type of event within a particular perimeter around the location of the calling terminal, the server prepares a message containing information on the type of event and on the location of the calling terminal.

Step 11: The server sends this message to the competent community within the particular perimeter around the location of the calling terminal. Various communication means can be used to transmit this message:

The server can request a standard voice server to call a telephone and to play a voice message when someone takes the call.

The server can request a standard SMS server to send an SMS message to a terminal capable of receiving SMS messages.

The server can request a standard instant messaging server to send a text message to a personal computer or other terminal capable of receiving instant messages.

Figure 2:
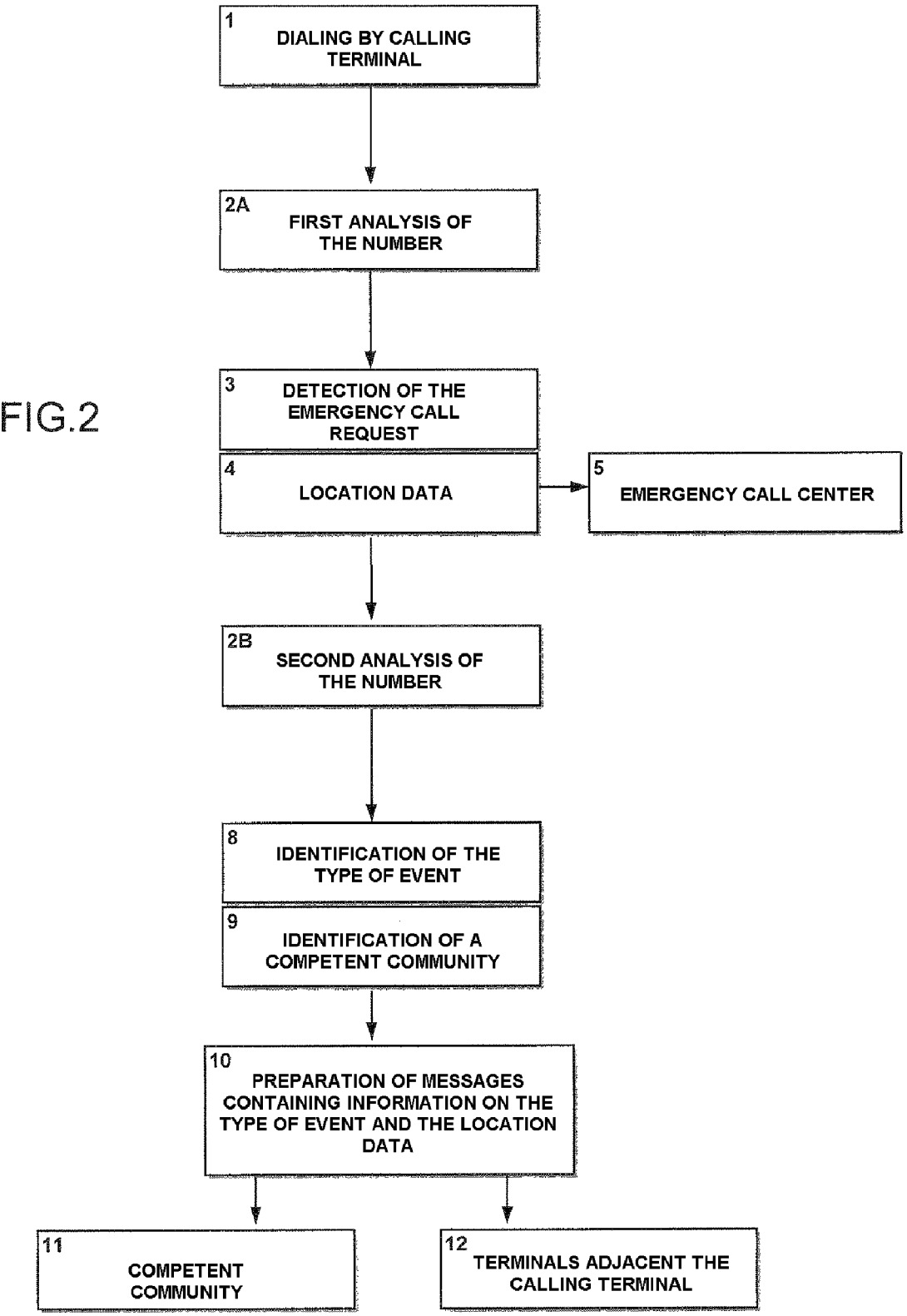
FIG. 2 is a diagram analogous to FIG. 1 and illustrating a different embodiment of the method of the invention.

FIG. 2 is a diagram analogous to that of FIG. 1, and illustrating a different embodiment of the method of the invention. The steps 1 to 11 are unchanged. During a supplementary step 12, message preparation means broadcast text or voice messages to all terminals situated within a particular perimeter around the location of the calling terminal, advantageously with an acknowledgement request. These messages can be IP MULTICAST (Internet Protocol Multicast) messages to terminals situated within a particular perimeter around the location of the calling terminal. The content of the message (text or audio) can dissuade witnesses to an event already reported to the emergency call center from calling the center. The risk of saturation of the call center is reduced commensurately. The message can also reassure other victims within the perimeter of the event already reported. The message can also reassure persons in the vicinity of the site of the event, and advise them what to do to guarantee their own safety.

A computer program determines the perimeter within which persons may be located, in particular participants in or witnesses to the event reported by the caller.

An operator or a voice synthesizer device produces a message (voice, text, multimedia) to be sent to such persons.

In the case of a call to an emergency call center, this message might be expressed in the following manner, for example: "[summary of the event known to the call center]. If you do not need help yourself, please do not call the emergency call center, as other people may need to contact us".

The message is advantageously updated. It is broadcast within the updated perimeter concerned only for a predetermined time.

The invention locates persons best able to intervene because of their proximity to the call site and their skills.

The invention does not affect the usual routing of calls to call centers, for example emergency call centers. It can be implemented in a call server by means of a program implementing the method of the invention.

The invention claimed is:

1. Method of communication between a calling terminal and an emergency call center via a call server to which said calling terminal and other terminals are connected, this method including:

a step (1, 2A, 2B) of the server receiving a request from a calling terminal to set up a call between the calling terminal and an emergency call center, and a step (5) of setting up a call between the calling terminal and the call center;

characterized in that it further includes:

a step (2B, 8) of identifying, in the call set-up request, a type of event belonging to a list of predefined event types;

a step (9) of identifying, in a set of communities with predefined capabilities and each having at least one terminal connected to said server, a community having capabilities suited to the type of event identified; and a step (11) of sending information to at least one terminal belonging to the community thus identified.

2. Method according to claim 1, characterized in that it further includes sending (11) at least one terminal belonging to the community thus identified the location of the calling terminal and the type of event identified.

3. Method according to claim 1, characterized in that the step (1, 2A, 2B) of the server receiving a request to set up a call between a calling terminal and an emergency call center includes a sub-step (2A) of analyzing a first portion of the called number, identifying a call to an emergency call center, and a sub-step (2B) of analyzing a second portion of the called number, identifying an event type (8).

4. Method according to claim 2, characterized in that it further includes sending (12) a message to all terminals within a particular perimeter around the location of the calling terminal.

5. Communication method according to claim 2, characterized in that the calling terminal is mobile and the location data includes geolocation data obtained by at least one of the following methods: identification of a cell or a sector, estimation of the time of arrival (TOA Time of Arrival, EOTD Enhanced Observed Time Difference TDOA), estimation of angles of arrival (AOA) or estimation of angles of incidence.

6. Communication method according to claim 2, characterized in that the calling terminal is a mobile, in particular a GSM or UMTS mobile, provided with a satellite navigation receiver, such as a GPS, GLONASS or GALILEO receiver.

7. Communication server including:
  means for receiving (1, 2A, 2B) a request from a calling terminal to set up a call between the calling terminal and an emergency call center, and
  means for setting up (5) a call between the calling terminal and the call center;
characterized in that it further includes:
  means for identifying (2B, 8), in the call set-up request, a type of event belonging to a list of predefined event types;
  means for identifying (9), in a set of communities with predefined capabilities and each having at least one terminal connected to said server, a community having capabilities suited to the type of event identified; and
  means for sending (11) information to at least one terminal belonging to the community thus identified.

8. Server according to claim 7, characterized in that it further includes means for receiving (4) the location of the calling terminal and the means for sending (11) information include means for sending the location of the calling terminal and the type of event identified.

9. Programmable device including storage means storing a program including instructions which execute the steps of the method according to claim 1 when they are executed.

10. Storage means storing a program including instructions which execute the steps of the method according to claim 1 when they are executed.

* * * * *